United States Patent
Hesl et al.

(10) Patent No.: US 9,655,569 B2
(45) Date of Patent: May 23, 2017

(54) MEDICAL IMAGING DEVICE WITH A GRIPPING MODULE

(71) Applicants: Stefan Hesl, Eschenbach (DE); Jürgen Plannerer, Kemnath (DE)

(72) Inventors: Stefan Hesl, Eschenbach (DE); Jürgen Plannerer, Kemnath (DE)

(73) Assignee: Siemens Aktiengesellschaft, München (DE)

( * ) Notice: Subject to any disclaimer, the term of this patent is extended or adjusted under 35 U.S.C. 154(b) by 168 days.

(21) Appl. No.: 14/502,334

(22) Filed: Sep. 30, 2014

(65) Prior Publication Data

US 2015/0092926 A1  Apr. 2, 2015

(30) Foreign Application Priority Data

Oct. 1, 2013 (DE) .................. 20 2013 008 489 U

(51) Int. Cl.
*A61B 6/00* (2006.01)
*A61B 6/04* (2006.01)

(52) U.S. Cl.
CPC .............. *A61B 6/0457* (2013.01); *A61B 6/04* (2013.01); *A61B 6/4233* (2013.01); *A61B 6/485* (2013.01)

(58) Field of Classification Search
CPC .................................... A61B 6/4405
See application file for complete search history.

(56) References Cited

U.S. PATENT DOCUMENTS

| | | | |
|---|---|---|---|
| 2006/0018431 A1 | 1/2006 | Kanemitsu | |
| 2008/0159486 A1 | 7/2008 | Hesl et al. | |
| 2009/0003520 A1 | 1/2009 | Kanemitsu et al. | |
| 2011/0182408 A1 | 7/2011 | Graf et al. | |
| 2012/0114106 A1 | 5/2012 | Dippl et al. | |
| 2015/0035257 A1* | 2/2015 | Zaid ....................... | B62K 3/002 280/641 |

FOREIGN PATENT DOCUMENTS

| | | |
|---|---|---|
| CN | 1723850 A | 1/2006 |
| CN | 101060810 A | 10/2007 |
| CN | 101143098 A | 3/2008 |
| CN | 101219055 A | 7/2008 |
| CN | 102133104 A | 7/2011 |
| CN | 102551753 A | 7/2012 |
| CN | 203000962 U | 6/2013 |
| CN | 203107141 U | 8/2013 |
| CN | 203852363 U | 10/2014 |

OTHER PUBLICATIONS

Chinese office Action for related Chinese Application No. 201410460798.8 dated Oct. 9, 2016, with English Translation.

* cited by examiner

Primary Examiner — Hoon Song
(74) Attorney, Agent, or Firm — Lempia Summerfield Katz LLC

(57) ABSTRACT

A medical imaging device includes a gripping module having at least a first holding grip and a second holding grip. The first holding grip and the second holding grip are configured for holding by a patient during an image recording. A control unit is arranged on the medical imaging device. The control unit is configured to control an automatic movement of the holding grips. As a result, manual operation of the holding grips by medical operators may be avoided, thereby simplifying and accelerating the process of recording images.

16 Claims, 2 Drawing Sheets

MEDICAL IMAGING DEVICE WITH A GRIPPING MODULE

RELATED APPLICATIONS

This claims the benefit of German Patent Application No. DE 202013008489.8, filed Oct. 1, 2013. The entire contents of the priority document are hereby incorporated herein by reference.

TECHNICAL FIELD

The present teachings relate generally to medical imaging devices that include a gripping module.

BACKGROUND

X-ray systems with X-ray detectors in the structural form of a vertically arranged flat-panel detector are used in horizontal recordings (e.g., thorax X-ray recordings). A patient to be examined is situated between an X-ray emitter and an X-ray detector that captures the X-rays. The X-ray emitter and the X-ray detector are aimed at the body region of the patient to be X-rayed. In order to image various body regions, the X-ray emitter and detector may be vertically displaceable.

In conventional wall buckies, the X-ray emitter is vertically displaceable via movement mechanics arranged on the ceiling. The X-ray detector is arranged on a column that is placed on the ground and fixed to the wall. The X-ray detector is vertically displaceable in terms of height using guiding rails via dedicated movement mechanics. The vertical movement of the X-ray detector may be carried out via a motorized drive and manually. During the X-ray recording, the patient stands in front of the X-ray detector. The X-ray emitter is aimed at the patient, such that the body region to be X-rayed is captured. With specific X-ray recordings or fluorographs (e.g., recordings of the thorax), the patient may grip holding grips in order to assume a body position that is suitable for the recording. FIG. 1 shows an example of a wall bucky having a column 1 on which a vertically displaceable X-ray detector 2 is arranged. On the rear side of the X-ray detector 2, a gripping module having two holding grips 3 is arranged (only one holding grip 3 is shown in FIG. 1). A patient may hold on to the holding grips 3 during an X-ray recording. The holding grips 3 are mounted on the X-ray detector 2, such that the holding grips are foldable. When, in order to achieve a technically correct X-ray recording, the holding grips 3 are to be firmly held by a patient, the holding grips 3 are individually folded out by an operator from a folded-back position. In some systems, the holding grips 3 may be attached to the X-ray detector 2 and removed after the X-ray recording is complete.

SUMMARY AND DESCRIPTION

The scope of the present invention is defined solely by the appended claims, and is not affected to any degree by the statements within this summary.

The present embodiments may obviate one or more of the drawbacks or limitations in the related art. For example, in some embodiments, a medical imaging device that includes a gripping module is provided.

A medical imaging device with a gripping module in accordance with the present teachings has at least a first holding grip and a second holding grip (e.g., at least two holding grips). The first holding grip and the second holding grip are configured such that a patient may firmly hold on to the first holding grip and the second holding grip during an image recording. A control unit is arranged on the medical imaging device. The control unit is configured to control an automatic movement of the first holding grip and the second holding grip. As a result, manual operation of the holding grips by a medical operator may be avoided, thereby simplifying and accelerating the process of recording images.

In some embodiments, a medical imaging device includes a gripping module having at least a first holding grip and a second holding grip (e.g., at least two holding grips). The first holding grip and the second holding grip are configured such that a patient may firmly hold on to the first holding grip and the second holding grip during an image recording. The imaging device includes a coupling unit connecting the first holding grip and the second holding grip. The coupling unit is arranged inside the gripping module and is configured such that, when the first holding grip is moved manually, the second holding grip also moves.

In some embodiments, the movement may be a folding-out movement or a folding-back movement. The holding grips may be folded out for an X-ray recording and folded back into a starting position after the X-ray is taken.

In addition, the movement may be adaptable to an image-recording program. For example, the medical imaging device may include an image-recording program that may store corresponding X-ray recording techniques for the individual organs. For each X-ray recording technique, a determination may be made as to whether the holding grips are to be used for the recording. For an X-ray recording, an operator of the imaging device chooses the corresponding image-recording program. The control unit evaluates the associated X-ray recording technique and, indirectly, controls the automatic pivoting of the holding grips. As a result, medical operators may no longer be tasked with the folding of the holding grips. In addition, a scenario in which an operator of the imaging device forgets to pivot the holding grips back after the X-ray is taken—thus limiting the movement of the X-ray device for safety reasons—may be avoided.

In some embodiments, the gripping module may be arranged in or on an X-ray detector.

The holding grips may be folded away in the X-ray detector, thereby reducing the danger posed by protruding holding grips.

In some embodiments, the holding grips may be configured in the shape of brackets or rods.

In some embodiments, the imaging device may be a radiography device or a fluoroscopy device.

DETAILED DESCRIPTION

Figure 1:
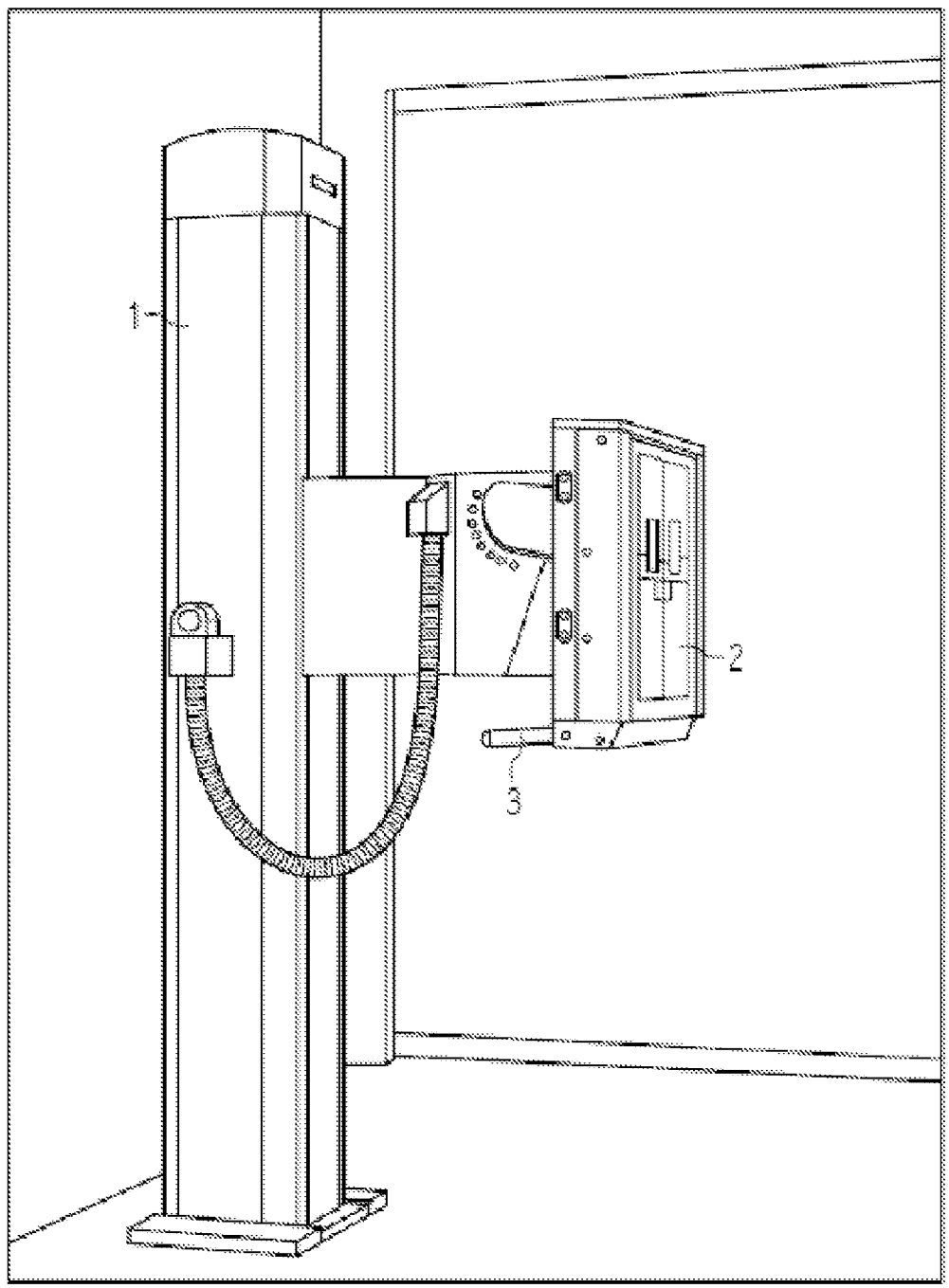
FIG. 1 shows a perspective view of a conventional wall bucky.
Figure 2:
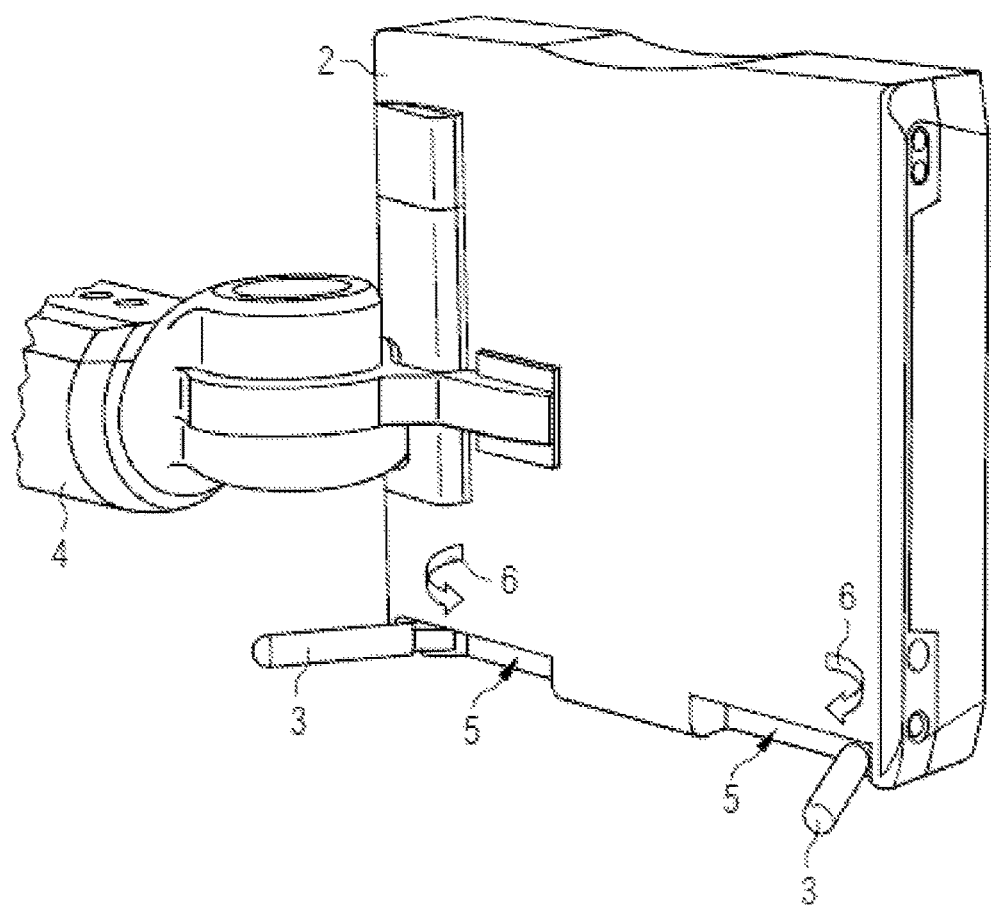
FIG. 2 shows a perspective view of an example of an X-ray detector with holding grips that may be folded away.

FIG. 2 shows an example of an X-ray detector with holding grips that may be folded away. A gripping module having a first holding grip 3 and a second holding grip 3 is arranged on an X-ray detector 2. The X-ray detector 2 is movably mounted to a detector support arm 4. When the first holding grip 3 and the second holding grip 3 are not going to be used for taking an X-ray, the first holding grip 3 and the second holding grip 3 are in the folded-back state and are folded away in a first grip recess 5 and a second grip recess 5, respectively, inside the X-ray detector 2. FIG. 2 shows the first holding grip 3 and the second holding grip 3 in a folded-out state. The first holding grip 3 and the second holding grip 3 may be automatically folded out of the first grip recess 5 and the second grip recess 5, respectively, for an image recording wherein the patient is to firmly hold on to the first holding grip 3 and the second holding grip 3. The automatic folding out of the first holding grip 3 and the second holding grip 3 may be controlled by a control unit (not shown) based on an image-recording program of the imaging device. In other embodiments, the first holding grip 3 and the second holding grip 3 may be manually folded out by an operator of the imaging device. For example, the operator may fold one of the first holding grip 3 and the second holding grip 3 out of its respective grip recess 5. Using a coupling unit (not shown) arranged in the gripping module, the other of the first holding grip 3 and the second holding grip 3 moves at the same time and is folded out of its respective recess 5. After the image is taken, the first holding grip 3 and the second holding grip 3 are automatically folded away by the control unit in the first recess 5 and the second recess 5, respectively. As an alternative to automatic control of the folding-back of the first holding grip 3 and the second holding grip 3, an operator may manually fold back the first holding grip 3 and the second holding grip 3. In such embodiments, it may be sufficient to manually fold back only one of the first holding grip 3 and the second holding grip 3 since, due to the coupling unit, the other of the first holding grip 3 and the second holding grip 3 is configured to move at the same time. The reference character 6 shown in FIG. 2 depicts directions of rotation for folding back the first holding grip 3 and the second holding grip 3, respectively. Once in the folded-back state, the first holding grip 3 and the second holding grip are folded away in the first recess 5 and the second recess 5, respectively, and do not protrude.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The invention claimed is:

1. A medical imaging device comprising:
a gripping module comprising a first holding grip and a second holding grip, the first holding grip and the second holding grip being individually configured for holding by a patient during an image recording; and
a control unit configured to control an automatic movement of the first holding grip and the second holding grip based on an image-recording program.

2. A medical imaging device comprising:
a gripping module comprising a first holding grip and a second holding grip, the first holding grip and the second holding grip being individually configured for holding by a patient during an image recording; and
a coupling unit connecting the first holding grip and the second holding grip;
wherein the coupling unit is arranged inside the gripping module;
wherein the coupling unit is configured such that a manual movement of the first holding grip results in a movement of the second holding grip; and
wherein the gripping module is arranged in or on an X-ray detector.

3. The imaging device of claim 1, wherein movement of the first holding grip and the second holding grip comprises a folding-back movement or a folding-out movement.

4. The imaging device of claim 1, wherein the gripping module is arranged in or on an X-ray detector.

5. The imaging device of claim 1, wherein the first holding grip and the second holding grip are configured to be folded away in the an X-ray detector.

6. The imaging device of claim 1, wherein the first holding grip and the second holding grip are configured in the shape of brackets or rods.

7. The imaging device of claim 1, wherein the imaging device is a radiography device or a fluoroscopy device.

8. The imaging device of claim 2, wherein movement of the first holding grip and the second holding grip comprises a folding-back movement or a folding-out movement.

9. The imaging device of claim 8, wherein movement of the first holding grip and the second holding grip is adaptable to an image-recording program.

10. The imaging device of claim 3, wherein the gripping module is arranged in or on an X-ray detector.

11. The imaging device of claim 2, wherein the first holding grip and the second holding grip are configured to be folded away in the X-ray detector.

12. The imaging device of claim 3, wherein the first holding grip and the second holding grip are configured to be folded away in an X-ray detector.

13. The imaging device of claim 4, wherein the first holding grip and the second holding grip are configured to be folded away in the X-ray detector.

14. The imaging device of claim 2, wherein the first holding grip and the second holding grip are configured in the shape of brackets or rods.

15. The imaging device of claim 2, wherein the imaging device is a radiography device or a fluoroscopy device.

16. A medical imaging device comprising:
an X-ray detector
a gripping module comprising a first holding grip and a second holding grip, the first holding grip and the second holding grip being individually configured for holding by a patient during an image recording; and
a coupling unit connecting the first holding grip and the second holding grip;
wherein the coupling unit is arranged inside the gripping module;
wherein the coupling unit is configured such that a manual movement of the first holding grip results in a movement of the second holding grip; and
wherein the first holding grip and the second holding grip are configured to be folded away in the X-ray detector.

* * * * *